US008652818B2

(12) United States Patent
Lawton, Jr. et al.

(10) Patent No.: US 8,652,818 B2
(45) Date of Patent: Feb. 18, 2014

(54) METHOD FOR EXTRACTING PROTEIN FROM A FERMENTATION PRODUCT

(75) Inventors: John Warren Lawton, Jr., Sioux Falls, SD (US); Jason Alan Bootsma, Sioux Falls, SD (US); Stephen Michael Lewis, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 940 days.

(21) Appl. No.: 12/651,401

(22) Filed: Dec. 31, 2009

(65) Prior Publication Data

US 2010/0178675 A1    Jul. 15, 2010

Related U.S. Application Data

(60) Provisional application No. 61/196,720, filed on Dec. 31, 2008, provisional application No. 61/207,868, filed on Dec. 31, 2008, provisional application No. 61/161,313, filed on Mar. 18, 2009, provisional application No. 61/161,318, filed on Mar. 18, 2009, provisional application No. 61/161,322, filed on Mar. 18, 2009, provisional application No. 61/161,325, filed on Mar. 18, 2009.

(51) Int. Cl.
*C12P 7/06* (2006.01)
*C12P 7/08* (2006.01)
*C12P 7/10* (2006.01)
*C12P 7/14* (2006.01)

(52) U.S. Cl.
USPC ........... 435/161; 435/162; 435/163; 435/165; 435/813

(58) Field of Classification Search
None
See application file for complete search history.

(56) References Cited

U.S. PATENT DOCUMENTS

| | | | |
|---|---|---|---|
| 2,133,591 A | 10/1938 | Swallen | |
| 3,535,305 A | 10/1970 | Carter et al. | |
| 5,580,959 A | 12/1996 | Cook et al. | |
| 6,602,985 B1 | 8/2003 | McInnis et al. | |
| 6,610,831 B1 | 8/2003 | McInnis et al. | |
| 7,045,607 B2 | 5/2006 | Cheryan | |
| 8,236,929 B2 * | 8/2012 | Cheryan et al. | ............... 530/373 |
| 2005/0239181 A1 | 10/2005 | Lewis et al. | |
| 2007/0089356 A1 | 4/2007 | Krasutsky et al. | |

OTHER PUBLICATIONS

Wolf, et al. "Isolation and Characterization of Zein from Corn Distillers' Grains and Related Fractions." Cereal Chemistry, vol. 74, No. 5, 1997. pp. 530-536.
Lawton. "Isolation of Zein Using 100% Ethanol." Cereal Chemistry, vol. 83, No. 5, 2006. pp. 565-568.
International Search Report mailed Mar. 5, 2010, for PCT Application Serial No. PCT/US09/69969, 4 pages.
Written Opinion mailed Mar. 5, 2010 for PCT Application Serial No. PCT/US09/69969, 8 pages.

* cited by examiner

*Primary Examiner* — Debbie K Ware
(74) *Attorney, Agent, or Firm* — Turocy & Watson, LLP

(57) ABSTRACT

A method of producing bioproducts from a feedstock in a system configured to produce ethanol and distillers grains from a fermentation product is disclosed. A system configured to process feedstock into a fermentation product and bioproducts including ethanol and meal is disclosed. A bioproduct produced from a fermentation product produced from a feedstock in a biorefining system is disclosed.

62 Claims, 14 Drawing Sheets

BEER COMPOSITION (percent)

| CONVENTIONAL FERMENTATION | | | | as is | dry |
|---|---|---|---|---|---|
| | Ethanol | pH | Solids | Protein | Protein |
| Average | 19.4 | 4.09 | 12.8 | 4.40 | 34.4 |
| Experiment 1 & 2 | 20.0 | 4.03 | 12.9 | 4.3 | 33.4 |

| RAW STARCH FERMENTATION (706) | | | | as is | dry |
|---|---|---|---|---|---|
| | Ethanol | pH | Solids | Protein | Protein |
| Average | 19.5 | 3.78 | 11.9 | 3.89 | 32.7 |
| Experiment 3 & 4 | 19.9 | 3.77 | 12.7 | 4.16 | 32.9 |

| ENDOSPERM FERMENTATION (708) | | | | as is | dry |
|---|---|---|---|---|---|
| | Ethanol | pH | Solids | Protein | Protein |
| Average | 18.3 | 4.24 | 9.30 | 4.01 | 43.1 |
| Experiment 5 & 6 | 17.9 | 3.67 | 8.43 | 3.35 | 39.8 |

FIG. 7A

WET CAKE COMPOSITION (percent)

| RAW STARCH FERMENTATION | | |
|---|---|---|
| Moisture | Sulfur* | Protein* |
| 69.1 | 0.67 | 31.0 |

* Average composition, percent of dry matter

FIG. 7B

DRIED SOLIDS COMPOSITION (percent)

| CONVENTIONAL FERMENTATION | | |
|---|---|---|
| Moisture | Sulfur* | Protein* |
| 9.40 | 0.83 | 27.9 |

| RAW STARCH FERMENTATION (716) | | |
|---|---|---|
| Moisture | Sulfur* | Protein* |
| 8.4 | 0.99 | 28.5 |

| ENDOSPERM FERMENTATION (718) | | |
|---|---|---|
| Moisture | Sulfur* | Protein* |
| 7.5 | 0.84 | 42.2 |

* Average composition, percent of dry matter

FIG. 7C

Zein Extraction Operating Conditions

|  | Typical Range | Preferred | Most Preferred |
|---|---|---|---|
| Solvent to Solids Ratio | 4:1 – 10:1 | 4:1 – 7:1 | 5:1 |
| Solvent Ethanol Concentration | 40 – 90 percent | 50 – 80 percent | 60 – 70 percent |
| Sodium Hydroxide Concentration | 0 – 7.0 percent | 2.8 – 4.0 percent | 3.2 – 3.8 percent |
| Temperature | 20 – 78 degrees Celsius | 50 – 75 degrees Celsius | 68 – 70 degrees Celsius |
| Extraction Time | 20 – 120 minutes | 25 – 60 minutes | 28 – 30 minutes |

FIG. 10

Zein Extraction Operating Conditions (1100)

Solvent to solids ratio (weight of solvent relative to weight of solids): (1102)

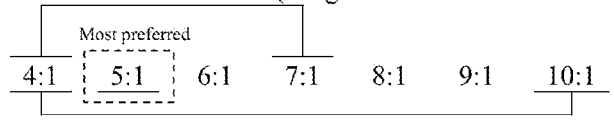

Solvent to solids concentration for zein extraction from beer: (1104)

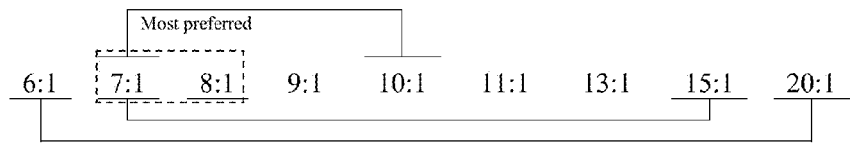

Solvent Ethanol Concentration (weight percent concentration of ethanol in extraction solvent): (1106)

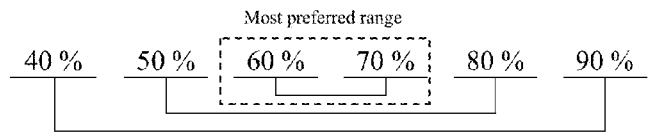

Sodium Hydroxide Concentration (weight percent of solids on a dry basis): (1108)

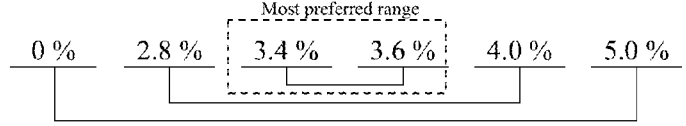

Extraction temperature (temperature of the slurry in the extraction vessel): (1110)

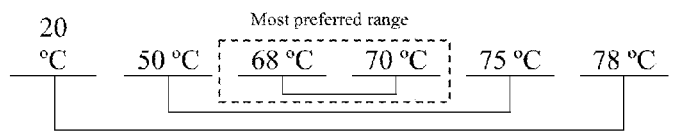

Extraction time (duration of time slurry is held at extraction temperature): (1112)

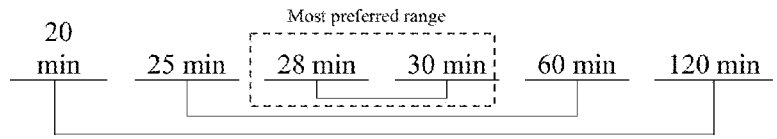

FIG. 11

Zein Extraction Yield from Different Starting Materials

|  | Beer | Wet Cake | DDG |
|---|---|---|---|
| Conventional Fermentation | 4.71 g | 5.59 g | 3.21 g |
| Raw Starch Fermentation | 6.90 g | 5.91 g | 6.29 g |
| Endosperm Raw Starch Fermentation | 7.98 g | 8.24 g | 8.35 g |

Yield and Composition of Zein Extracted from Different Starting Materials

| Exp. | Beer Sample from | NaOH* | Zein recovered (g) dry basis | Protein dry basis % | Fat dry basis % | α-zein content % | β and γ- zein content % |
|---|---|---|---|---|---|---|---|
| 1 | Conventional fermentation | No | 3.75 | 78.4 | 18.9 | 100 | 0 |
| 2 |  | Yes | 5.95 | 82.4 | 17.1 | 85.0 | 15.0 |
| 3 | Raw starch fermentation | No | 3.25 | 73.6 | 19.5 | 98.7 | 1.3 |
| 4 |  | Yes | 6.25 | 82.9 | 12.2 | 74.8 | 25.2 |
| 5 | Endosperm raw starch fermentation | No | 4.55 | 79.5 | 16.1 | 100 | 0 |
| 6 |  | Yes | 9.05 | 82.9 | 9.0 | 74.1 | 25.9 |

\* Extraction agent

FIG. 14A

| Sample | Protein dry basis % | Fat dry basis % | α-zein content % | β and γ- zein content % |
|---|---|---|---|---|
| Average | 90.1 | 1.5 | 79.4 | 20.6 |
| Low | 80.7 | 0.1 | 74.2 | 16.5 |
| High | 98.8 | 7.5 | 83.5 | 25.8 |
|  |  |  |  |  |

FIG. 14B

| Sample | Protein dry basis % | Fat dry basis % | α-zein content % | β and γ- zein content % |
|---|---|---|---|---|
| Average | 88.2 | 1.1 | 84.6 | 15.4 |
| Low | 82.2 | 0.1 | 82.8 | 12.1 |
| High | 91.6 | 7.64 | 87.9 | 17.2 |
|  |  |  |  |  |

FIG. 14C

Effect of Homogenization and Temperature on Zein Extraction Recovery

|  | 30 min stirred<br>50 degrees Celsius<br>70 percent ethanol<br>3.5 percent NaOH | 3 min homogenized<br>70 degrees Celsius<br>70 percent ethanol<br>3.5 percent NaOH |
|---|---|---|
|  | Recovery, percent of theoretical | Recovery, percent of theoretical |
| Conventional Fermentation | 52 % | 63 % |
| Raw Starch Fermentation | 57 % | 89 % |
| Endosperm Raw Starch Fermentation | 64 % | 75 % |

FIG. 15

Zein Gelling Time at Different Temperatures

| | | Storage Temperature, degrees Celsius | | |
|---|---|---|---|---|
| | | 5 °C | 22 °C | 40 °C |
| Extraction starting material | High Protein Distillers Dried Grains (DDG-HP) | 90-120 days | 24 days | 12 days |
| | Corn Gluten Meal (CGM) | 90-120 days | 17 days | 10 days |
| | CGM Top Phase | - | 38 days | - |
| | CGM Bottom Phase | - | < 1 day | - |

FIG. 16

METHOD FOR EXTRACTING PROTEIN FROM A FERMENTATION PRODUCT

CROSS-REFERENCE TO RELATED APPLICATIONS

The present application claims the priority of and expressly incorporates by reference the following applications: (a) U.S. Provisional Patent Application No. 61/196,720 entitled "EXTRACTION OF ZEIN FROM FERMENTED CORN" which was filed Dec. 31, 2008 (as U.S. patent application Ser. No. 12/347,566); (b) U.S. Provisional Patent Application No. 61/207,868 entitled "EXTRACTION OF ZEIN FROM FERMENTING FRACTIONATED CORN" which was filed Dec. 31, 2008 (as U.S. patent application Ser. No. 12/347,743); (c) U.S. Provisional Patent Application No. 61/161,313 entitled "EXTRACTION OF ZEIN FROM FERMENTED CORN" which was filed Mar. 18, 2009; (d) U.S. Provisional Patent Application No. 61/161,318 entitled "EXTRACTION OF ZEIN FROM FERMENTING FRACTIONATED CORN" which was filed Mar. 18, 2009; (e) U.S. Provisional Patent Application No. 61/161,322 entitled "ZEIN EXTRACTION AND RECOVERY" which was filed Mar. 18, 2009; and (f) U.S. Provisional Patent Application No. 61/161,325 entitled "ZEIN EXTRACTION AND RECOVERY" which was filed Mar. 18, 2009.

GOVERNMENT INTERESTS

The Government may have rights in an invention claimed in the present application pursuant to Contract No. DE-FG36-08GO8033 with the Department of Energy.

TECHNICAL FIELD

The present application relates to a system for the extraction of protein from a fermentation product. The present application also relates to a system for the extraction of zein from fermented solids in the production of ethanol from corn. The present application further relates to a composition of extracted zein comprising alpha-zein, beta-zein, and gamma-zein.

BACKGROUND

Zein is a group of plant proteins that can be extracted from corn or corn-protein-containing substrates, such as corn gluten meal. Zein is classified as GRAS (Generally Recognized As Safe) by the U.S. Food and Drug Administration and has a variety of commercial uses including the manufacture of edible food packaging, edible films, biodegradable plastic resins, chewing gum base, tablet-coating compounds, adhesives, coatings for paper cups, soda bottle cap linings, etc. Zein can also be processed into resins and other bioplastic polymers, which can be extruded or rolled into a variety of plastic products. Zein has utility as a raw material for a variety of non-toxic and renewable polymer applications.

Zein belongs to a class of proteins called prolamins, soluble in alcohol. Zein comprises approximately forty to fifty percent of the total protein in corn, or about four percent of the corn kernel. Zein has been further divided into four subclasses: alpha-zein, beta-zein, gamma-zein, and delta-zein. Alpha-zein is the primary commercially used zein and accounts for about seventy percent of the zein in corn. Beta-zein accounts for about five percent of zein in corn. Gamma-zein accounts for approximately twenty to twenty-five percent of zein in corn and delta-zein accounts for about one to five percent of zein. Each zein type (alpha, beta, gamma, and delta) has a different amino-acid profiles and exhibits slightly different properties. Zein can be extracted and recovered from corn or co-products from corn processing.

Corn gluten meal, a by-product of ethanol production by wet milling, is a typical starting material for zein extraction because its protein content is sixty percent or greater. Sulfur dioxide or other chemicals that may be used during the preparation (e.g., in a steeping process) of corn gluten meal may adversely affect zein quality.

Ethanol can be produced from grain-based feedstocks (such as corn), cellulosic feedstocks (such as switchgrass or corn cobs), or other plant material (such as sugar cane). Ethanol production from corn produces fermentation products (e.g., co-products) that are suitable for use as starting materials for zein extraction.

In a wet milling process ethanol is produced from corn by first steeping the corn kernels in water that contains sulfur dioxide, and then separating the kernels into endosperm, fiber and germ. The endosperm is further processed to produce starch and corn gluten, which can be dried into corn gluten meal. Corn gluten meal may comprise at least sixty percent protein, and is typically used as a starting material for zein extraction in commercial zein production. The sulfur dioxide or other chemicals that may be used during the preparation of corn gluten meal may adversely affect zein quality.

Ethanol can also be produced from corn using a dry-milling process. In a dry-milling process, a starch containing material, such as corn, is ground into flour and is slurried with water and enzymes. The slurry may be cooked to liquefy the starch and to facilitate saccharification. Additional enzymes may be added to complete saccharification to break down the starch into simple sugars (e.g. glucose) that can be fermented using an ethanologen (e.g. yeast). The fermentation produces a fermentation product that comprises a liquid portion or component and a solids portion or component. The liquid portion comprises ethanol and water and soluble components. The residual solids comprise for example proteins, fiber, oil, and other insoluble components.

The fermentation product comprising a liquid component and a solids component may be distilled to separate ethanol and whole stillage (e.g. wet solids or fermentation solids). Whole stillage comprises residual solids and water, and may be further separated into wet cake and thin stillage. Wet cake (wet solids) can be dried into meal such as dried distillers grains (DDG); thin stillage can be reduced to syrup and added to the wet cake or meal during the drying process to produce dried distillers grains with solubles (DDGS). Meal such as DDG and DDGS can be used as an animal feed product According to an alternative process, for example as described in U.S. Patent Application Publication No. 2005/0239181, starch may be converted into sugars and fermented in a raw-starch process without "cooking" or liquefaction. Heat damage to proteins and other components of the slurry may be avoided by using the raw-starch process.

A dry fractionation process that does not utilize sulfur dioxide may be used instead of wet milling to fractionate the corn into endosperm, fiber and germ. The amount of residual solids in the fermentation product can be reduced by fractionation and by eliminating fiber and germ, both low in starch, from fermentation. Endosperm is primarily comprised of starch and protein with small amounts of fiber and oil present. Zein is also concentrated in the endosperm; more than half of the endosperm protein may be comprised of zein. When endosperm is fermented, the residual solids comprise a high concentration of zein. The dried residual solids from endosperm fermentation are high in protein and result in a meal that is called "high protein dried distiller grains" (DDG HP).

Distillers dried grains (DDG) contain zein, but a high percentage or high quality of zein may not be recovered, if the product has been subject to chemical treatments or heat.

It would be advantageous to provide for a system for extracting protein from a fermentation product. It would also be advantageous to provide for a method of producing bioproducts from a feedstock in a system configured to produce ethanol and distillers grains from a fermentation product. It would also be advantageous to provide for a system configured to process feedstock into a fermentation product and bioproducts including ethanol and meal. It would also be advantageous to provide for a bioproduct produced from a fermentation product produced from a feedstock in a biorefining system.

SUMMARY

The present invention relates to a method of producing bioproducts from a feedstock in a system configured to produce ethanol and distillers grains from a fermentation product. The method comprises the steps of processing the feedstock into a starch-containing component and creating a slurry comprising the starch-containing component. The method comprises the steps of preparing the starch-containing component of the slurry into a fermentable component for fermentation and fermenting at least a portion of the fermentable component of the slurry into the fermentation product. The method comprises the steps of processing the fermentation product into bioproducts comprising the ethanol and the distillers grains and producing a bioproduct comprising a zein composition from the fermentation product.

The present invention relates to a system configured to process feedstock into a fermentation product and bioproducts including ethanol and meal. The system comprises a mill for processing the feedstock into a starch-containing component so that a slurry comprising the starch-containing component can be formed. The system also comprises a vessel configured to contain the slurry and for fermentation of a fermentable component of the starch-containing component into the fermentation product. The system comprises a distillation system for recovery of ethanol from the fermentation product and separation of wet solids matter from the fermentation product to be dried into the meal. System comprises a system for extracting a bioproduct comprising a zein composition from the fermentation product. The fermentation product comprises a protein component and the zein composition comprises at least a portion of the protein component of the fermentation product.

The present invention relates to bioproduct produced from a fermentation product produced from a feedstock in a biorefining system. The bioproduct comprises a zein composition comprising alpha zein and beta zein and gamma zein. The zein composition has been extracted from a protein component of the fermentation product.

DESCRIPTION OF THE DRAWINGS

FIG. 5A is a process flow for zein extraction using a milling process. FIG. 5B is a process flow for zein extraction using a fractionation process.

FIG. 6A is a process flow for zein extraction from raw starch endosperm beer. FIG. 6B is a process flow for zein extraction from wet cake.

FIGS. 7A through 7C are tables of the average composition of fermented solids. FIG. 7A is a table of beer composition for conventional, raw starch, and endosperm fermentation. FIG. 7B is a table of a wet cake composition for raw starch fermentation. FIG. 7C is a table of dried solids (DDG) composition for conventional, raw starch, and endosperm fermentation.

FIG. 10 is a table for the operating conditions and parameters for a zein extraction vessel.

FIG. 11 is a graphical representation of parameters and operating conditions for a zein extraction process.

FIGS. 14A through 14C are tables for composition of zein that provide data from experimental extractions. FIG. 14A is a table for the composition of zein extracted from beer at laboratory scale. FIG. 14B is a table for the composition of zein extracted from high protein distillers dried grains at laboratory scale. FIG. 14C is a table for the composition of zein extracted from high protein distillers dried grains at pilot scale.

FIG. 15 is a table of the effect of homogenization and temperature.

FIG. 16 is a table for zein gelling time at different storage conditions of zein solutions extracted from different starting materials.

FIG. 17A is a graph of the viscosity of zein that was extracted from high protein distillers dried grains. FIG. 17B s a graph of the viscosity of zein that was extracted from corn gluten meal.

DESCRIPTION OF THE EMBODIMENTS

Figure 1:
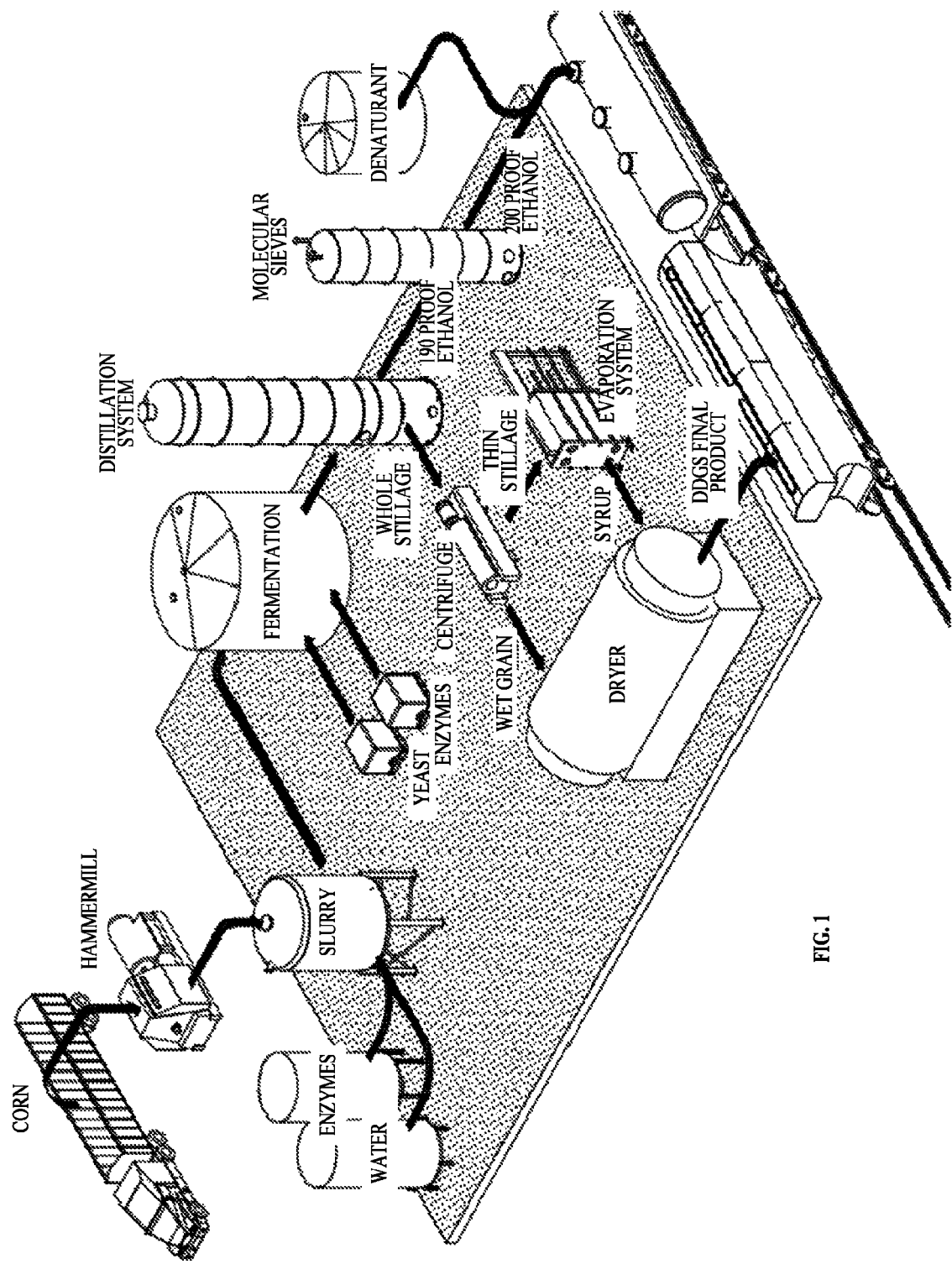
FIG. 1 is a schematic diagram of an ethanol production facility.

FIG. 1 is a schematic block diagram of an ethanol plant. A method of producing bioproducts from a feedstock in a system configured to produce ethanol and distillers grains from a fermentation product can be used in the ethanol plant. The ethanol plant can comprise a system configured to process feedstock into a fermentation product and bioproducts including ethanol and meal. The plant comprises a facility for producing corn-based ethanol and zein can be extracted from fermentation solids, a component of the fermentation product. The fermentation solids may comprise beer, beer solids, wet solids, wet cake, or dry solids, meal distillers grains, (e.g., DDG, DDGS, DDG HP). The ethanol plant can utilize various systems and methods, such as conventional starch liquefaction (e.g., cooked starch or raw starch hydrolysis, among other processes) to process corn (or other types of biomass).

Figure 2A:
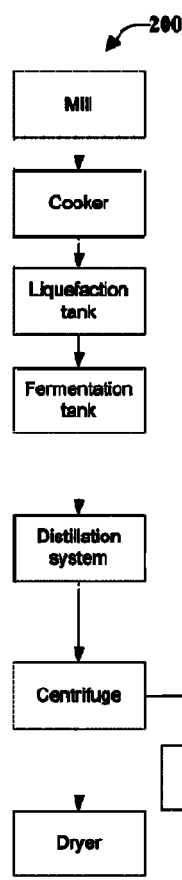
FIGS. 2A through 2C are schematic block diagrams of an ethanol production facility.
Figure 2B:
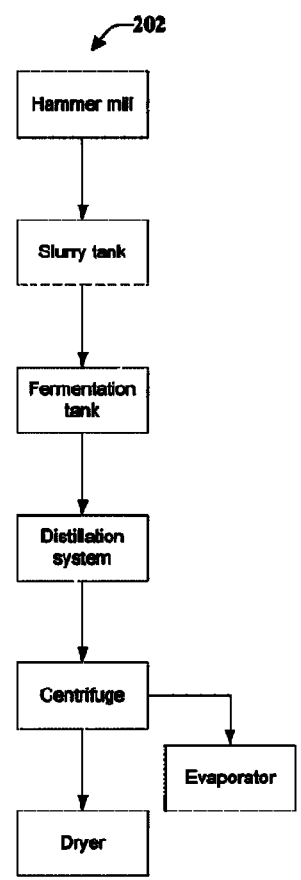
Figure 2C:
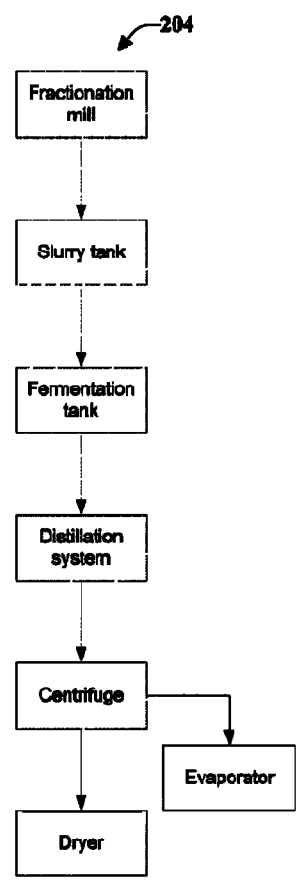

FIGS. 2A through 2C are schematic block diagrams of an ethanol production facility. FIG. 2A is a schematic block diagram of a system for a facility using a conventional "cooked starch" fermentation process 200. In a "cooked starch" ethanol plant producing ethanol from corn, corn kernels are processed to separate the starch-containing material (e.g., endosperm) from other matter (such as fiber and germ). The starch-containing material is then slurried with water and liquefied to facilitate saccharification where the starch is converted into sugar (glucose) and fermentation where the sugar is converted by an ethanologen (yeast) into ethanol. The product of the fermentation (fermentation product) is beer that comprises a liquid component and a solids component. A process typically used in a conventional ethanol plant, the liquefaction of the starch-containing material is performed by "cooking" the slurry at temperature at or above the gelatinization temperature of the starch (typically at or above 60-75 deg C.).

FIG. 2B is a schematic block diagram of a system for a facility using a "raw starch" fermentation process. In "raw starch" fermentation, starch may be converted and fermented without "cooking" or liquefaction (as in the "cooked starch" process). FIG. 2C is a schematic block diagram of a system for a facility using a raw starch endosperm fermentation process 204. In raw starch endosperm fermentation process, the corn kernel is fractionated into endosperm, germ and fiber. The fractionation process is intended to separate the starch-containing endosperm from the germ and fiber (which are low in starch). The endosperm is then supplied to the "raw starch" fermentation process.

Figures 3A, 3B, 3C:
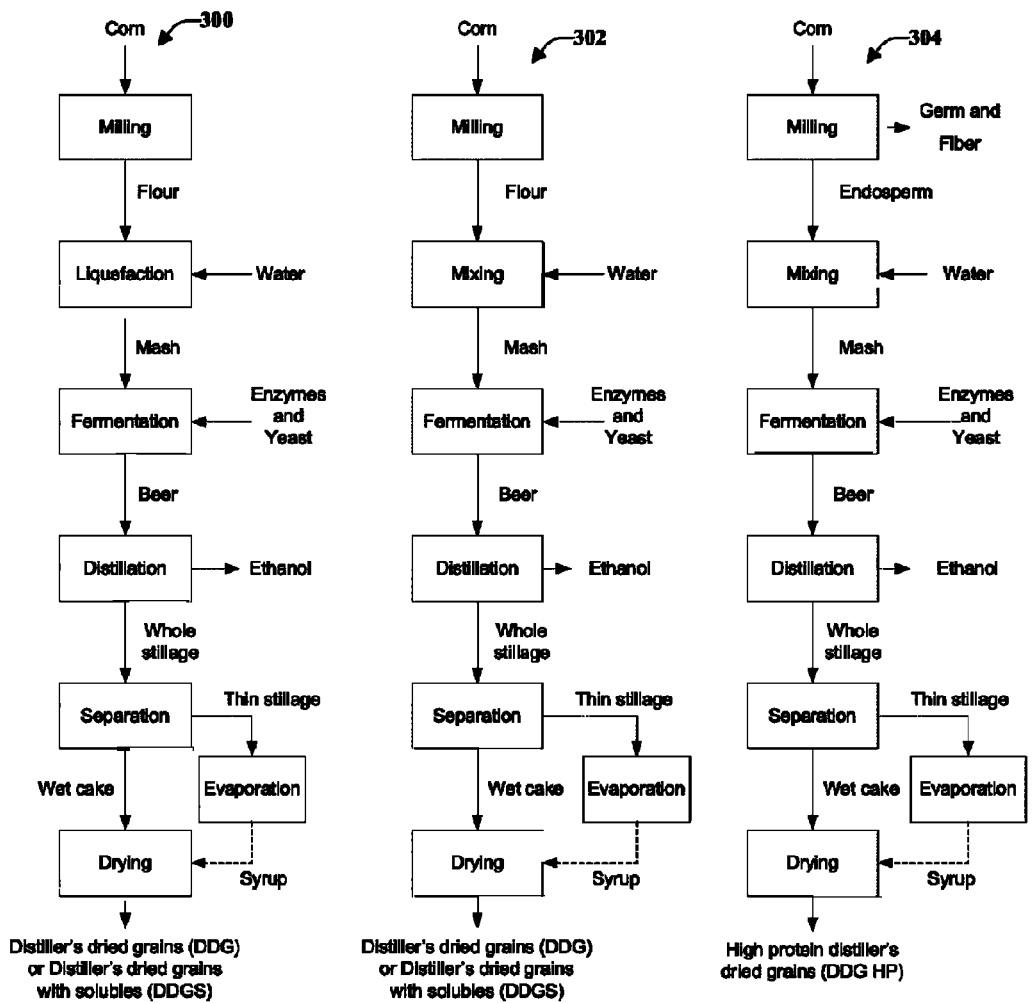
FIGS. 3A through 3C are process flow diagrams of an ethanol production process.

FIGS. 3A through 3C are process flow diagrams of an ethanol production process. FIG. 3A is a process flow diagram of a process for conventional ethanol production 300 and corresponds to FIG. 2A where distillers dried grains (DDG) or distillers dried grains with solubles (DDGS) are the result of the cooked starch fermentation. FIG. 3B is a process flow diagram of a process for ethanol production that comprises the step of raw starch hydrolosis 302 and corresponds to FIG. 2B where DDG or DDGS are the result of the raw starch fermentation. FIG. 3C is a process flow diagram of a process for raw starch endosperm ethanol production 304 and corresponds to FIG. 2C where high protein distillers dried grains (DDG HP) is the result of the raw starch endosperm fermentation.

Figure 4:
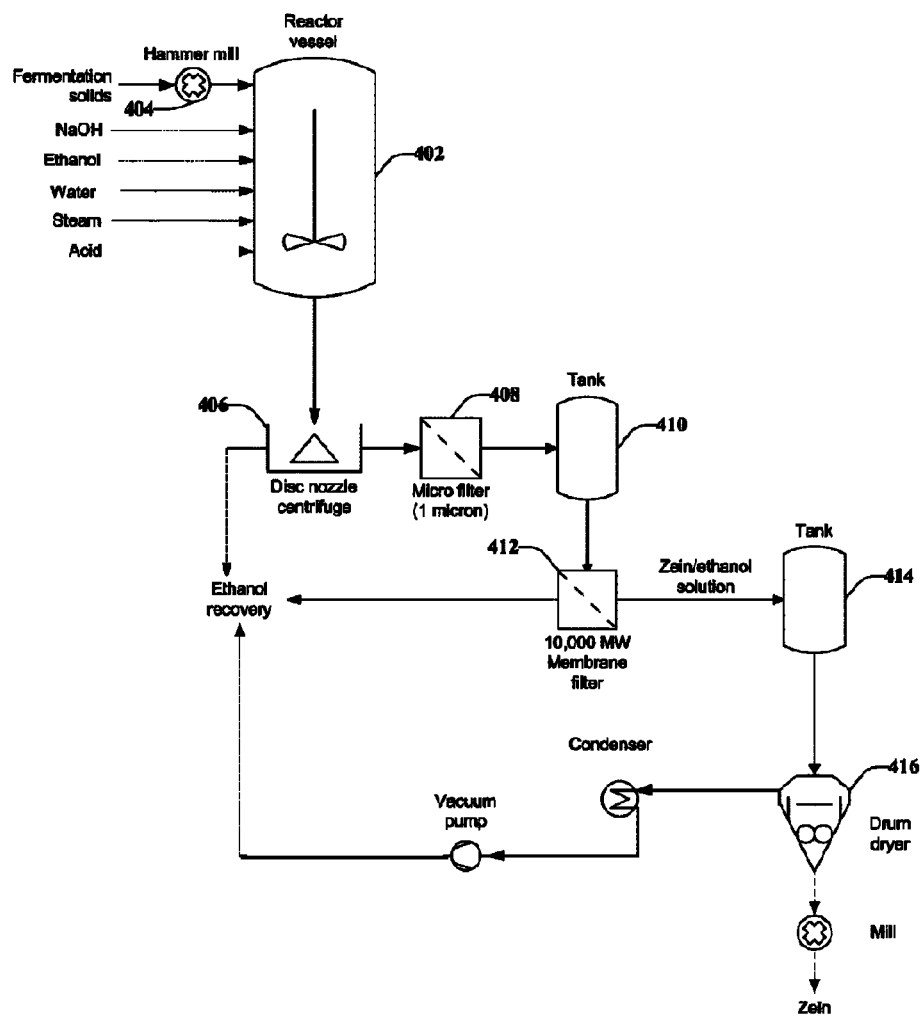
FIG. 4 is a schematic block diagram of the equipment used in an ethanol production facility comprising a system for extracting zein from fermented solids.

The equipment used in an ethanol production facility for zein extraction from fermented solids (e.g., DDG HP, DDGS, DDG, beer, and wet cake) is illustrated in FIG. 4. Substantially the same equipment is utilized for each of the different fermentation processes (conventional, raw starch, raw starch endosperm) and for each of the different starting materials (fermented solids, DDG HP, DDGS, DDG, beer, wet cake). According to an exemplary embodiment, the feedstock utilized is DDG HP. According to another embodiment, the feedstock used could be DDG.

According to an exemplary embodiment, the zein extraction and recovery process may comprise three steps: extraction, refinement (e.g., purification), and recovery. The extraction step removes zein by solubilization; zein is soluble in aqueous alcohol. The extraction equipment comprises a reactor vessel 402 into which are input fermentation solids (which can be processed through a hammer mill 404); the fermentation solids are the output of the various ethanol processes shown in FIGS. 3A through 3C.

Other inputs to the reactor vessel 402 comprise sodium hydroxide (NaOH, optional), alcohol, water, steam, and acid (optional). According to certain embodiments, the alcohol can be selected from an alcohol composition comprising C1 to C7 alcohols (e.g., methanol, ethanol, or propanol). According to certain embodiments, the alcohol is ethanol.

According to an exemplary embodiment, the aqueous alcohol (or aqueous ethanol) solution comprises an extraction agent, such as sodium hydroxide in an amount based on the dry solids of the starting material. According to an exemplary embodiment, up to 7.0 percent of sodium hydroxide is used. According to a preferred embodiment, the concentration of sodium hydroxide is 2.8-4.0 percent. According to the most preferred embodiment, the concentration of sodium hydroxide is 3.2-3.8 percent.

According to an embodiment, the contents of the reactor vessel 402 are drained into a centrifuge, such as a disc nozzle centrifuge 406 (or basket centrifuge), for separation into a solids component and a liquid component comprising ethanol and zein. Zein can be refined by filtration and recovered from the liquid component by drying or precipitation.

As illustrated, the refinement or purification step may comprise the use of multiple filters (or membranes) configured to remove matter having different sizes (e.g., membrane filters having different pore sizes). The first filter 408 can have, for example, one micrometer pore size (e.g., a micro filter). The first filter 408 is designed to protect the ultra filtration membrane by removing suspended solids that were not removed in the separation step. The solids are sent to a tank 410 and the liquids are further processed to recover the zein. The liquids are then passed over a second filter 412, which can be a membrane filter with a 10,000 molecular weight cutoff intended to remove small molecular weight components and to concentrate the zein solution. The retentate (e.g., zein/ethanol solution) is sent to a holding tank 414 (vessel or mixing reactor) and the permeate is further processed for ethanol recovery (e.g., by distillation).

Zein is recovered from the retentate solution (e.g., from the second filter 412) by drying the solution (for example with a vacuum double drum dryer 416 or a desolventizer). In accordance with certain embodiments, the zein solution can be precipitated by diluting the alcohol concentration to where zein is no longer soluble (e.g., 50 percent (w/v) or less).

In an embodiment, zeolite can be utilized to remove impurities from the zein composition. A crude solution of a zein contained in an aqueous alcohol solvent is contacted with a zeolite adsorbent under conditions effective for adsorption of the color and odor impurities in the zein solution onto the zeolite. The treated solution may be separated from the adsorbent with the intent to recover high quality zein dissolved in the aqueous alcohol solvent. Optionally, more impurities (e.g., residual color or order) can be removed by contacting the treated solution with an activated carbon adsorbent or a mixture of activated carbon and zeolite adsorbents. The process can be conducted using batch, semi-continuous, or continuous systems.

Figure 5A:
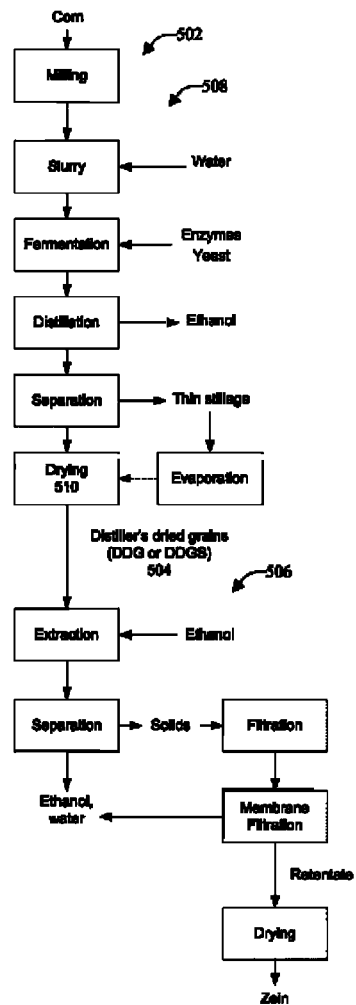
FIGS. 5A through 5B are process flow diagrams of a system for extraction of zein from raw starch dry solids (DDG) and raw starch endosperm dry solids (DDG HP).
Figure 5B:
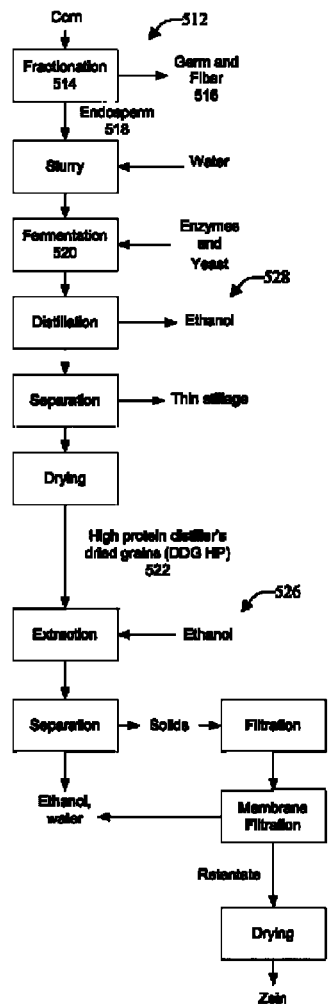

FIGS. 5A through 5B illustrate process flow diagrams for zein extraction from dry solids (DDG) and endosperm dry solids (DDG HP) from a raw starch fermentation process. FIG. 5A illustrates a process flow 502 for zein extraction from a raw starch fermentation process (e.g., without using fractionation). The DDG or DDGS 504 is used for zein extraction and recovery 506 can come from the ethanol production process 508 after the drying step 510. FIG. 5B illustrates a process flow 512 for zein extraction with fractionation 514. During fractionation 514, the corn germ and fiber 516 are separated from the endosperm 518 and removed, leaving the endosperm 518 for fermentation 520. The DDG HP 522 is used for zein extraction and recovery 524 after drying 526 in the ethanol production process 528.

Figures 6A, 6B:
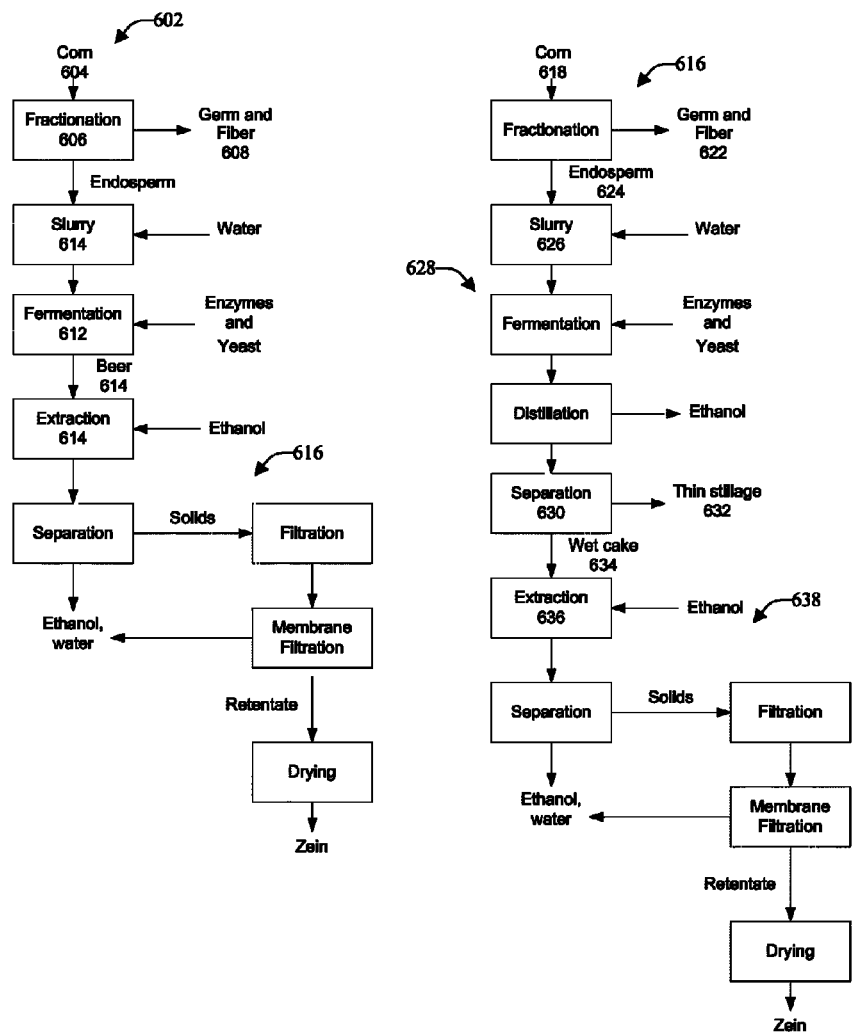
FIGS. 6A through 6B are process flow diagrams of a system for zein extraction.

FIGS. 6A through 6B illustrate process flow diagrams for zein extraction. FIG. 6A illustrates a process flow 602 for zein extraction from raw starch endosperm beer. In this case, the corn 604 is fractionated 606 to remove the germ and fiber 608, leaving the endosperm 610 for fermentation 612. A slurry 614 is created. The beer 614 is used for zein extraction and recovery 616 after fermentation. FIG. 6B illustrates a process flow 616 zein extraction from wet cake. As illustrated, the corn kernel 618 undergoes fractionation 620 to remove the germ and fiber 622 from the endosperm 624. A slurry 626 is created. The endosperm 624 is saccharified and fermented 628 into a fermentation product, such as beer that is separated 630 into a liquid component, shown as thin stillage 632, and a solids component, shown as comprising wet cake 634. The wet cake 634 is used for zein extraction 636 and recovery 638.

FIGS. 7A through 7C are tables of the average (representative for commercial production) composition of fermented solids (DDG, DDG HP, DDGS, beer, and wet cake), intended to be utilized as starting materials for zein extraction.

Figure 8:
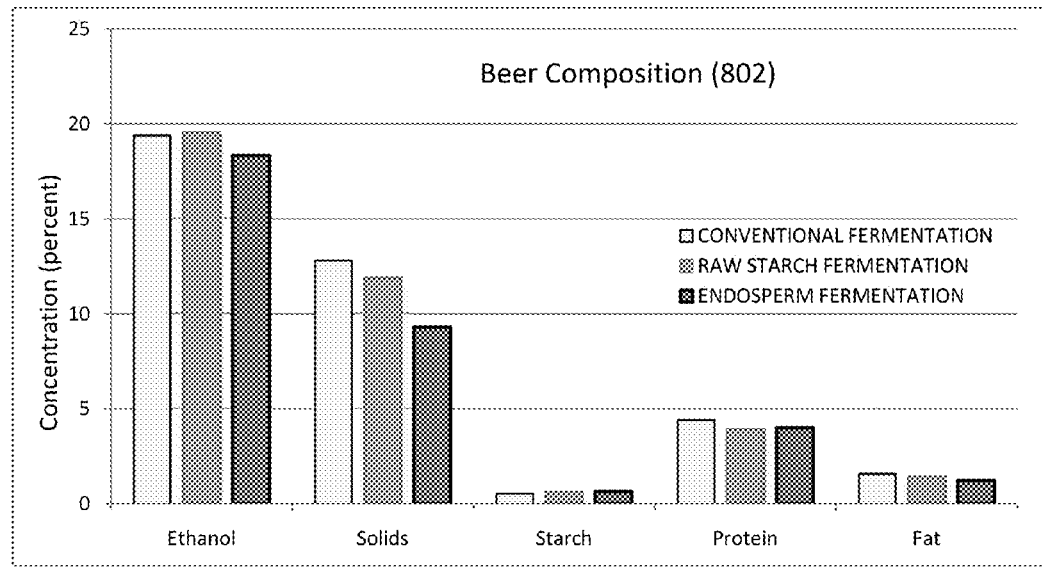
FIG. 8 is a chart for the average composition of beer in conventional, raw starch, and raw starch endosperm fermentations.

FIG. 7A is a table of beer composition and is also visually represented in FIG. 8, which illustrates a chart for the average composition of beer used in examples according to an exemplary embodiment. Data for beer from three different types of processes is displayed: conventional fermentation, raw starch fermentation, and endosperm fermentation. The numbers are on an "as is" condition. The beer composition and other information was collected from six experiments.

Wet cake composition for raw starch fermentation is illustrated in FIG. 7B. The average moisture content of the wet cake is 69.1 percent and protein content is 31.0 percent of dry matter.

FIG. 7C illustrates a table for dried solids (DDG) composition for conventional fermentation, raw starch fermentation, and endosperm fermentation. The sulfur content and protein content illustrated are the average composition as a percent of dry matter.

Figure 9:
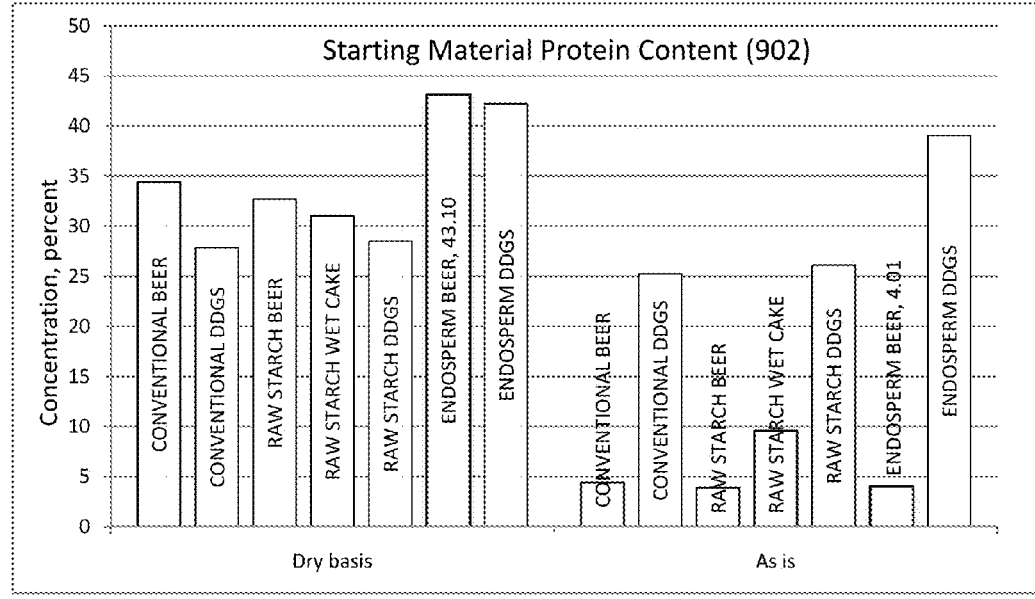
FIG. 9 is a chart for the average protein content in starting materials for zein extraction.

A chart for the average protein content 902 in starting materials for zein extraction is illustrated in FIG. 9. The protein content for each starting material is divided into two subsets, one for dry basis (left portion of the chart) and one for the starting material in an "as is" condition (right portion of the chart). As illustrated, the starting material can be conventional beer, conventional DDGS, raw starch beer, raw starch wet cake, raw starch DDGS, endosperm beer, and/or endosperm DDGS. The concentration values are represented as percentages.

FIG. 10 illustrates a table for the operating conditions and parameters for a zein extraction. A typical range, a preferred range, and a most preferred value or range is provided for each of a solvent to solids ratio, a solvent to solids ratio for beer, a solvent ethanol concentration, a sodium hydroxide concentration, a temperature, and an extraction time. A graphical representation of these parameters and operating conditions is illustrated in FIG. 11. The ranges of zein extraction parameters and operating conditions are shown using nested ranges. The typical range is represented by the outer identified values, the preferred range is identified by the inner identified values, and the most preferred value or range is identified within the dotted blocks.

The solvent to solids ratio 1102 is the weight of the solvent (combined ethanol and water) relative to the weight of the solids. A typical range of solvent to solids ratio is 4:1 through 10:1. A preferred range of solvent to solids ratio is 4:1 through 7:1. A most preferred solvent to solids ratio is 5:1.

For zein extraction from beer 1104, a typical range of solvent to solids ratio is 6:1 through 10:1. A preferred range of solvent to solids ratio is 7:1 through 10:1. A most preferred solvent to solids ratio is 7:1 through 8:1.

The solvent ethanol concentration 1106 is the weight percent concentration of ethanol in extraction solvent. A typical range for solvent ethanol concentration is 40 through 90 percent. A preferred range for solvent ethanol concentration is 50 through 80 percent. A most preferred range for solvent ethanol concentration is 60 through 70 percent.

The sodium hydroxide concentration 1108 is the weight of solids on a dry basis. A typical range for sodium hydroxide concentration is 0 percent through 5 percent. A preferred range is 2.8 percent through 4.0 percent. A most preferred range is 3.4 percent through 3.6 percent.

The extraction temperature 1110 is the temperature of the slurry in the extraction vessel. A typical temperature range for zein extraction is 20 through 78 degrees Celsius. A preferred temperature range for zein extraction is 50 through 75 degrees Celsius. A most preferred temperature range for zein extraction is 68 through 70 degrees Celsius.

The extraction time 1112 is the duration of time the slurry is held at the extraction temperature. A typical extraction time is 20 through 120 minutes. A preferred extraction time is 25 through 60 minutes. A most preferred extraction time is 28 through 30 minutes.

EXAMPLES

Experiments and tests were conducted to evaluate zein compositions and yields from different starting materials and processes. FIGS. 12 through 17 provide information related to the examples.

Figures 12, 13:
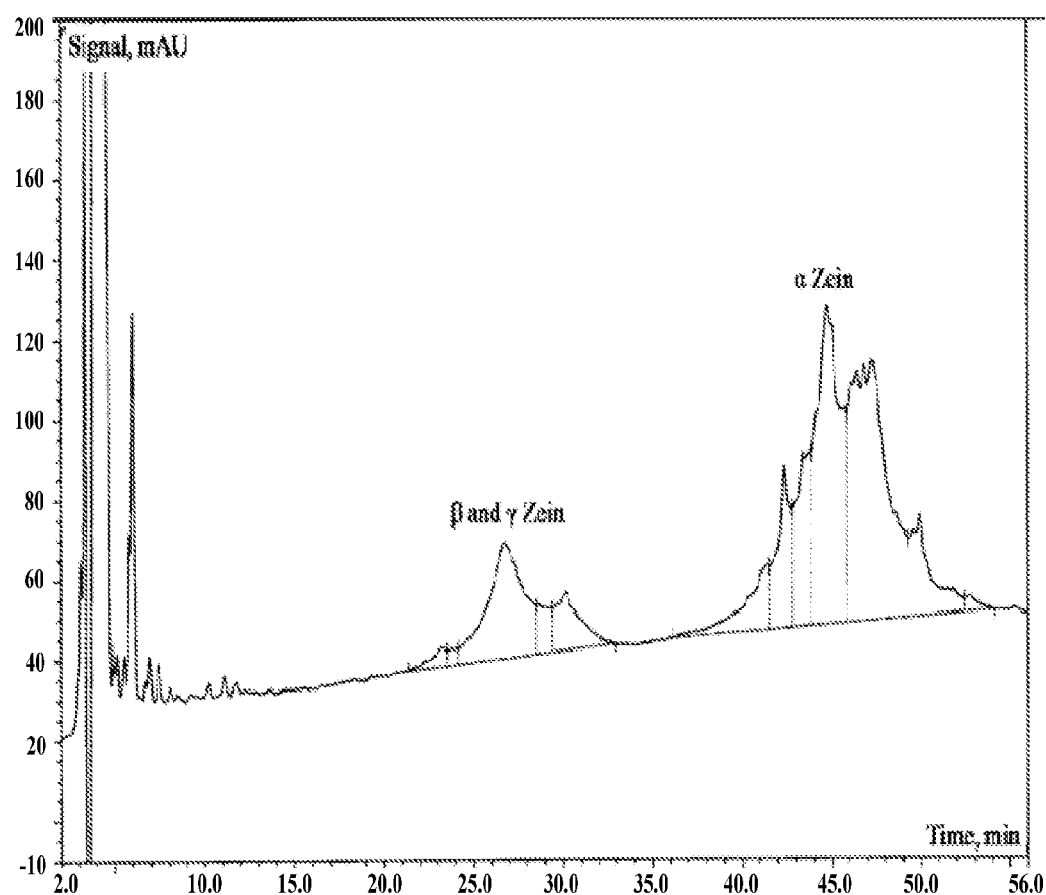
FIG. 12 is a table illustrating zein extraction yield from different starting materials.
FIG. 13 is an example chromatogram of zein composition.

According to a series of examples, zein composition was extracted from different starting materials (beer, wet cake, and DDG) from the different ethanol processes (cooked starch fermentation, raw starch fermentation, and endosperm raw starch fermentation) to compare the zein yields. Zein was extracted using 70 percent ethanol in water with 3.5 percent sodium hydroxide (based on the dry solids of the starting material) at 70 degrees Celsius for 30 minutes. FIG. 12 is a table illustrating the example zein extraction yields. Extracting from DDG (from raw starch fermentation) recovers more zein than does extracting from DDG from a "cooked starch" fermentation process (shown as "conventional fermentation"). The combination of corn fractionation and raw starch fermentation provides better extraction efficiencies (at best partially explained by the higher protein content of DDG HP).

FIG. 13 is an example of a HPLC chromatogram of zein extracted for DDG HP at laboratory scale. Shown are alpha-zein ($\alpha$ zein), beta zein ($\beta$ zein) and gamma zein ($\gamma$ zein). The peaks for beta and gamma-zein did not completely separate using this technique, and the relative amounts of beta and gamma are reported as a total sum of both types of zein.

Experiments were performed to study the yield and composition of zein extracted from different starting materials. FIGS. 14A through 14C are tables for composition of zein that detail the results of the yield and composition experiments.

Zein was extracted from beer at laboratory scale to study yield and composition of the extracted zein. FIG. 14A is a table of the composition of zein extracted from beer at laboratory scale. Six examples are illustrated by experiments with two experiments conducted for each process (conventional fermentation, raw starch fermentation, and endosperm raw starch fermentation). The starting material for these experiments is illustrated in the table of FIG. 7A. The data is from experimental extractions using solvent (ethanol) with ("YES") or without ("NO") sodium hydroxide (NaOH). If sodium hydroxide was not used, the beta-zein and gamma-zein content of the extracted/recovered zein was either zero or very close to zero, as shown in FIG. 14A. When sodium hydroxide was used, the beta-zein and gamma-zein content was much higher (up to around 25.9 percent in this example). The amount of zein recovered, in grams, dry basis was almost twice as much as the amount of zein recovered without the use of sodium hydroxide as shown in FIG. 14A. The alpha, beta, and gamma-zein composition of zein was obtained by analysis of reverse phase liquid chromatography (RP-HPLC) of zein.

A study was conducted to determine the yield and composition of zein extracted from high protein distillers dried grains at laboratory scale. The data is from experimental extractions using 70 percent ethanol with 3.5 percent sodium hydroxide (based on the dry solids of the starting material). The alpha, beta, and gamma-zein composition of zein was obtained by analysis of RP-HPLC chromatograms of zein. The results of the yield and composition of zein from high protein distillers dried grains at laboratory scale is shown in FIG. 14B.

The bioproduct comprises a zein composition comprising by dry weight basis a protein component of at least 70 percent by weight of the zein composition and a fat component of no more than 10 percent by weight. The protein component comprises the zein composition.

Zein was extracted from high protein distillers dried grains at pilot scale to study yield and composition of the extracted zein. The data is from pilot scale extractions using 77 kg of solvent and 15.4 kg dry DDG HP. According to an exemplary embodiment for extracting zein from DDG, the equipment used for the zein extraction and recovery comprise: an 80 liter reactor vessel for the extraction; a 48"×30" perforated basket centrifuge (commercially available from Sanborn Technologies of Walpole, Mass.) to separate the suspended solids from zein solution; a membrane filter containing a polyethersulfone 7.9" UF 10,000 molecular weight cut-off membrane (commercially available from Parker Hannifin of Cleveland, Ohio) to concentrate and remove impurities in the zein solution; and a 32"×72" Vacuum Double Drum Dryer (commercially available from Buflovak of Buffalo, N.Y.) to dry the zein from solution. The alpha, beta, and gamma-zein composition of zein was obtained by analysis of RP-HPLC chromatograms of zein. The yield and composition of the zein is shown in FIG. 14C.

Zein was extracted from beer to study the effect of homogenization and temperature on zein extraction recovery. According to an exemplary embodiment, the zein extraction method comprises fermented beer with 50 grams (dry basis) of solids mixed with enough ethanol to produce a 70 percent (w/w) aqueous ethanol solution. The mixture was further diluted with additional 70 percent (w/w) aqueous ethanol to produce an extraction mixture with a solvent to solids ratio of 9:1. The exact amount of ethanol and 70 percent aqueous ethanol needed for the extraction depended upon the water content of the beer solids.

Extractions were performed with the solvent either containing sodium hydroxide or not containing sodium hydroxide. If sodium hydroxide was used, 2.3 ml of a 50 percent (w/w) solution was added to the solvent prior to heating. The solvent and beer solids were heated separately in closed containers to 70 degrees Celsius in a water bath. The hot solvent and beer solids were mixed and then homogenized for 3 minutes using a Polytron Model PT-2100 homogenizer (available from Kinematica AG of Switzerland) on power setting 26.

After homogenizing, the mixtures were centrifuged using a Model IEC HN-SII centrifuge (available from International Equipment Co. of Needham Heights, Mass.) for 10 minutes at 5000 rpm. The solids component or fraction was air dried and retained for analysis. The liquid component or fraction (containing the zein) was neutralized to approximately pH 7 using either 6N hydrochloric acid or 50 percent (w/w) sodium hydroxide. The zein contained in the liquid fraction was recovered by precipitating the solution in excess cold water (approximately 0 degrees Celsius). Zein was removed from the water by centrifuging for 10 minutes at 4600 rpm using a Beckman Model J-6B centrifuge (available from Beckman Coulter Inc. of Brea, Calif.). The liquid was discarded and the zein was air dried and analyzed.

The results of the analysis is shown in FIG. 15, which is a table illustrating the effect of homogenization and temperature on zein extraction recovery. According to an embodiment, the extraction time can be reduced by homogenizing the material at 70 degrees Celsius. Two values for recovery, percent of theoretical are illustrated for each of conventional fermentation, raw starch fermentation, and endosperm raw starch fermentation. The first value for each is for 30 minutes stirred, 50 degrees Celsius, 70 percent ethanol, and 3.5 percent sodium hydroxide (based on the dry solids of the starting material). The second value is for 3 minutes homogenized, 70 degrees Celsius, 70 percent ethanol, and 3.5 percent sodium hydroxide (based on the dry solids of the starting material). Homogenizing the sample improves the extraction efficiency and can also reduce extraction time from 30 minutes to 3 minutes.

Zein gelling time at different temperatures was studied for different extraction starting materials. FIG. 16 illustrates a table for zein gelling time at different storage conditions of zein solutions extracted from different starting materials. Zein was extracted using 70 percent aqueous ethanol with 3.5 percent sodium hydroxide (based on the dry solids of the starting material) at 70 degrees Celsius for 20 minutes in a 50 liter reactor (available from Northland Stainless, Tomahawk, Wis.). The mixture was then centrifuged to remove solids in a 20 inch×9.5 inch basket centrifuge (available from Sanborn Technologies of Walpole, Mass.) fitted with a polymeric filter cloth with 50 micron openings. The liquid fraction containing zein was concentrated and purified by passing over a 10,000-molecular-weight-cut-off-ultra filtration membrane (available from Parker-Hannifin of Cleveland, Ohio).

The zein solution was split into three samples: one stored at room temperature (approximately 22 degrees Celsius), one stored at 5 degrees Celsius and one stored at 40 degrees Celsius. The viscosity of zein solutions was measured daily by pouring 300 milliliters of sample into a 600 milliliter Griffen beaker, and viscosity measurements were taken with a Brookfield Digital Viscosity Meter DV-I (available from Brookfield Engineering Laboratories of Middleboro, Mass.). Spindle 2 was used at 100 revolutions per minute to test solution viscosity. The viscosity of the samples was tested until the samples formed a gel.

Figure 17A:
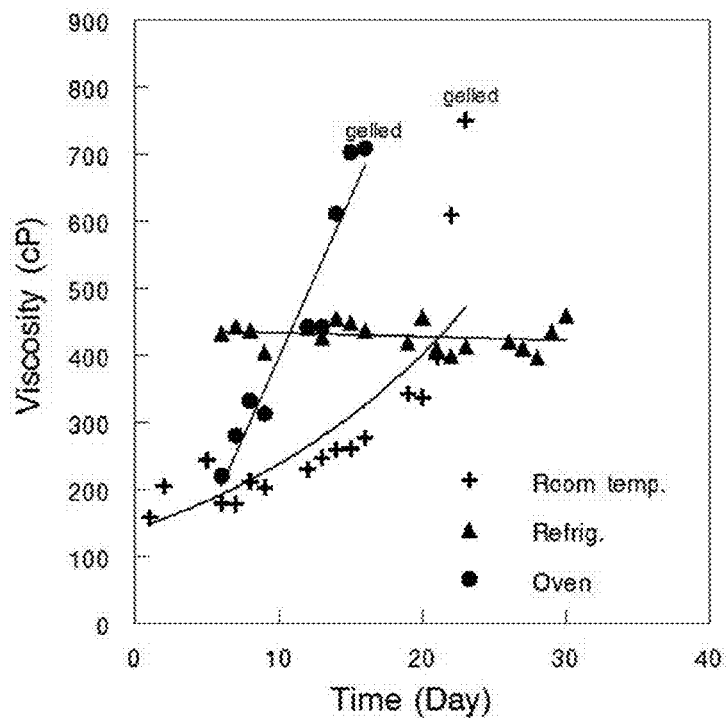
FIGS. 17A through 17B are graphs of zein viscosity over time at different temperatures.
Figure 17B:
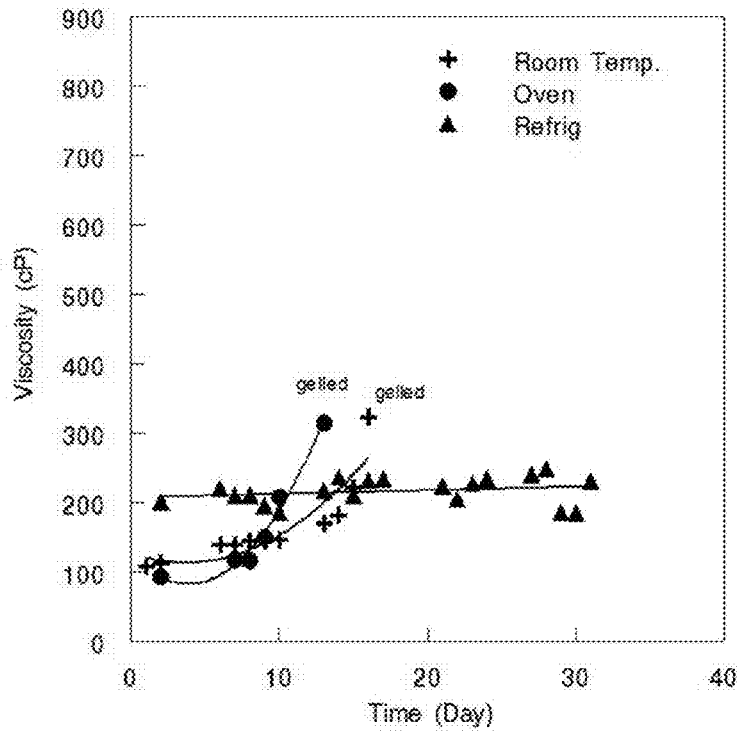

Zein viscosity over time at different temperatures was studied, as shown in FIGS. 17A though 17B. Viscosity in centipoises (cP) is shown along the vertical axis and time, represented in days, is shown along the horizontal axis. FIG. 17A illustrates viscosity of zein that was extracted from high protein distillers dried grains and FIG. 17B illustrates viscosity of zein that was extracted from corn gluten meal. Room temperature was 22 degrees Celsius, refrigerator temperature was 5 degrees Celsius and oven temperature was 40 degrees Celsius.

Preliminary viscosity tests on zein solutions showed them to be non-Newtonian and thixotropic. The zein solution extracted from corn gluten meal exhibited a lower viscosity (approximately 100 centipoise) than the zein solution extracted from the high protein distillers dried grains (approximately 200 centipoise), but the zein solution extracted from corn gluten meal gelled faster and after reaching a lower viscosity (17 days at room temperature and 10 days at 40 degrees Celsius, both approximately 300 centipoise) compared to the zein solution extracted from high protein distillers dried grains, which achieved viscosities of over 700 centipoise before gelling after 24 days at room temperature and 12 days at 40 degrees Celsius. This difference in viscosity may be a result of the zein solution extracted from corn gluten meal containing lower molecular weight zein peptides due to the potential damage caused by the sulfur dioxide employed during wet milling. Both zein solutions took three to four months to gel when stored at 5 degrees Celsius.

The two zein solutions also appeared visually different. While the zein solution extracted from the high protein distillers dried grains contained a single phase, the zein solution extracted from the corn gluten meal contained two phases, which were separable by laboratory centrifugation. When stored at room temperature, the bottom phase gelled in less than a day, while the top phase took approximately 38 days to gel.

According to other alternative embodiments producing the bioproduct comprises extracting the zein composition by applying a solvent composition to the fermentation product and separating the fermentation product with the solvent composition into the zein composition and a solids component. The solvent composition comprises an agent. The agent can comprise sodium hydroxide. The agent can comprise potassium hydroxide. The agent can comprise an acid. The agent can comprise a hydrochloric acid. The agent can comprise an extraction agent. The extraction agent can comprise an alkali hydroxide. The extraction agent can be sulfite. The extraction agent can comprise sodium metabisulfite. The extraction agent can comprise phiol. The extraction agent can comprise 2-mercaptoethanol.

In accordance with various embodiments, the concentrations of the various proteins of zein may be altered by processing to recover within the available range a zein intended to have a composition more specifically applicable to the intended commercial uses (such as by increasing the beta and gamma-zein percentage to allow for more usage in strength-requiring applications).

Conventional zein extraction methods utilize seventy percent aqueous ethanol to extract zein. The disclosed embodiments provide methods where the ethanol concentration is increased after extraction, preferably to ninety percent. As a result of increasing the percentage of ethanol, more beta-zein and gamma-zein can precipitate out of the zein solution.

Yields of recovered zein depend on time, temperature, particle size, and percent aqueous alcohol used for the extraction. Sodium hydroxide can also be added to the solvent to increase the zein yields. Using sodium hydroxide (e.g., as an extraction agent) in the solvent also changes the solubility of beta and gamma zein and enables the extraction of beta and gamma zein. Other extraction agents may also be used, such as another alkali hydroxide (e.g., potassium hydroxide), an acid (hydrochloric acid or sulfuric acid), or a sulfite (e.g., sodium sulfite, sodium bisulfate or sodium metabisulfite). The relative volumes of ethanol, extraction agent, and starting material will change based on the moisture content of the starting material and targeted ethanol concentration.

Zein recovery is improved by extracting at 50 degrees Celsius or higher and by the addition of 3.5 percent sodium hydroxide or another reducing agent to the aqueous alcohol. By increasing the pH of the extracting solvent using sodium hydroxide, zein recovery increases. Decreasing pH also increases the amount of material recovered, but the recovered material is lower in protein. Not adjusting the pH of the solvent extracted the least amount of zein.

The terms "dried distillers grains," "DDG," "dried distillers grains with solubles," "DDGS," "grains," "granular material," "pelletized material" or the like can refer to particulate matter. Although many types of biomass may be fermented in an alcohol plant producing various types of particulate products to be transported to other locations, a corn-based ethanol plant producing dried distillers' grains is discussed throughout this application for illustrative purposes of material properties and operational aspects for this invention.

The word "exemplary" is used to mean serving as an example, instance, or illustration. Any aspect or design described as "exemplary" is not necessarily to be construed as preferred or advantageous over other aspects or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

In view of the exemplary apparatus and methods, methodologies that may be implemented in accordance with the disclosed subject matter will be better appreciated with reference to the flowcharts of the various figures. While for purposes of simplicity of explanation, the methodologies were shown and described as a series of blocks, it is to be understood and appreciated that the claimed subject matter is not limited by the order of the blocks, as some blocks may occur in different orders and/or concurrently with other blocks from what is depicted and described. Moreover, not all illustrated blocks may be required to implement the methodologies.

It is important to note that the construction and arrangement of the elements of the disclosed subject matter as described in this application and as shown in the figures is illustrative only. Although some embodiments have been described in detail in this disclosure, those skilled in the art who review this disclosure will readily appreciate that many modifications are possible (e.g. variations in size, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures and combinations. Accordingly, all such modifications are intended to be comprised within the scope of the disclosed subject matter. Other substitutions, modifications, changes and omissions may be made in the design, operating conditions and arrangement of the exemplary embodiments without departing from the spirit of the present inventions.

We claim:

1. A method of producing bioproducts from a feedstock in a system configured to produce ethanol and distillers grains from a fermentation product comprising the steps of:
   (a) processing the feedstock into a starch-containing component;
   (b) creating a slurry comprising the starch-containing component;
   (c) preparing the starch-containing component of the slurry into a fermentable component for fermentation comprising liquefaction;
   (d) fermenting at least a portion of the fermentable component of the slurry into the fermentation product;
   (e) processing the fermentation product into bioproducts comprising the ethanol and the distillers grains; and
   (f) producing a bioproduct comprising a zein composition from the fermentation product including extracting the zein composition from the distillers grains in a single step extraction, and the zein composition comprises, by weight of zein in the zein composition, alpha zein in a percentage of at least 68 percent, beta zein and gamma zein in a combined percentage of at least 17 and no more than 25.9.

2. The method of claim 1 wherein the fermentation product comprises beer and the zein composition is extracted from the beer.

3. The method of claim 1 wherein the fermentation product comprises a liquid component and a solids component and the zein composition is extracted from the solids component.

4. The method of claim 1 wherein the fermentation product comprises ethanol and stillage.

5. The method of claim 4 wherein the stillage comprises whole stillage.

6. The method of claim 4 wherein the stillage comprises wet solids.

7. The method of claim 3 wherein the solids component of the fermentation product comprises wet solids.

8. The method of claim 3 wherein the solids component of the fermentation product comprises distillers grains.

9. The method of claim 6 wherein the wet solids comprise wet cake.

10. The method of claim 3 wherein the solids component comprises ethanol.

11. The method of claim 1 wherein the system comprises a distillation system to which the fermentation product is supplied and wherein the step of producing the bioproduct comprises extracting the zein composition after the fermentation product has been supplied to the distillation system.

12. The method of claim 1 wherein the step of producing the bioproduct comprises extracting the zein composition by (a) applying a solvent composition to the fermentation product and (b) separating the fermentation product with the solvent composition into the zein composition and a solids component.

13. The method of claim 1 wherein the fermentation product comprises fermentation solids and the step of producing the zein composition further comprises milling the fermentation solids; supplying the milled fermentation solids to a vessel; and wherein the fermentation solids are treated with a solvent composition in the vessel.

14. The method of claim 13 wherein the solvent composition comprises sodium hydroxide and treated fermentation solids are created in the vessel.

15. The method of claim 14 further comprising the step of separating the treated fermentation solids into a liquid component and a treated solids component.

16. The method of claim 15 further comprising the step of separating the treated solids component in a filtration system.

17. The method of claim 16 wherein the filtration system comprises a micro filter.

18. The method of claim 16 wherein the filtration system comprises a membrane filter.

19. The method of claim 16 wherein the filtration system produces a permeate and a retentate.

20. The method of claim 19 wherein the retentate comprises the zein composition.

21. The method of claim 19 wherein the permeate comprises ethanol.

22. The method of claim 12 wherein the solvent composition comprises ethanol.

23. The method of claim 13 wherein the pH of the solvent composition is adjusted in the vessel.

24. The method of claim 23 wherein the pH of the solvent composition is adjusted to a range of between 4 and 11.

25. The method of claim 12 wherein the solvent composition comprises ethanol and sodium hydroxide.

26. The method of claim 13 wherein heat is supplied to the vessel.

27. The method of claim 17 wherein the micro filter is configured to retain matter having a particle size of 0.5 to 2 micrometers.

28. The method of claim 18 wherein the membrane filter is configured with a 10,000 molecular weight cutoff.

29. The method of claim 12 wherein separating the fermentation product is performed in a separator.

30. The method of claim 29 wherein the separator is a centrifuge.

31. The method of claim 19 wherein the zein composition from the retentate of the filtration system is supplied to a dryer.

32. The method of claim 19 wherein the zein composition from the retentate of the filtration system is supplied to a desolventizer.

33. The method of claim 13 wherein the vessel is a mixing reactor.

34. The method of claim 1 wherein the feedstock is corn and the step of processing the feedstock comprises milling.

35. The method of claim 1 wherein the feedstock is corn and the step of processing the feedstock comprises fractionating the corn into endosperm, germ and fiber and the starch-containing component comprises endosperm substantially free of germ and fiber.

36. The method of claim 1 wherein the fermentation product comprises a protein component and the zein composition comprises at least a portion of the protein component of the fermentation product.

37. The method of claim 36 wherein the zein composition comprises alpha zein, beta zein, and gamma zein.

38. The method of claim 1 wherein the step of preparing the starch-containing component into the fermentable component comprises raw starch hydrolysis.

39. The method of claim 1 further comprising the step of drying the zein composition.

40. The method of claim 1 wherein the zein composition is produced without raising the temperature of the zein composition at any time during the fermentation process or extraction process above a temperature of about 75° C.

41. The method of claim 1 wherein none of the process steps comprise raising the temperature of the fermentation product above a temperature of about 45° C., and wherein the fermentation product is produced from a cold fermentation process.

42. The method of claim 1 wherein the step of preparing the starch-containing component into the fermentable component comprises raw starch hydrolysis and comprises saccharifying the starch-containing component of the feedstock at a temperature below a starch gelatinization temperature.

43. The method of claim 42 wherein the fermentation product comprises proteins from the feedstock that have not been substantially affected by heat.

44. The method of claim 43 wherein the proteins comprise the zein composition.

45. The method of claim 12 wherein the solvent composition comprises an agent.

46. The method of claim 45 wherein the agent comprises an extraction agent.

47. The method of claim 46 wherein the extraction agent comprises an alkali hydroxide.

48. The method of claim 46 wherein the agent comprises at least 0.5 percent sodium hydroxide.

49. The method of claim 46 wherein the agent comprises potassium hydroxide.

50. The method of claim 46 wherein the agent comprises an acid.

51. The method of claim 46 wherein the agent comprises a hydrochloric acid.

52. The method of claim 46 wherein the extraction agent is sulfite.

53. The method of claim 51 wherein the extraction agent comprises sodium metabisulfite.

54. The method of claim 51 wherein the extraction agent comprises phiol.

55. The method of claim 54 comprises 2-mercaptoethanol.

56. The method of claim 13 wherein steam is supplied to the vessel.

57. The method of claim 36 wherein the zein composition comprises beta zein and gamma zein.

58. The method of claim 52 wherein the fermentation product comprises solids and sodium hydroxide is provided in a range of up to about 5 percent of the solids.

59. The method of claim 26 wherein the fermentation product in the vessel is heated to a temperature no greater than 75 degrees Celsius.

60. The method of claim 1 wherein the step of producing the zein composition comprise the steps of extraction, refinement, and recovery.

61. The method of claim 60 wherein the refinement comprises purification of the zein composition.

62. The method of claim 46 wherein the agent comprises at least 2.8 percent sodium hydroxide.

* * * * *